United States Patent [19]

Abushanab

[11] Patent Number: 5,491,146
[45] Date of Patent: Feb. 13, 1996

[54] HYDROXYLATED ERYTHRO-HYDROXYNONYLADENINES AND RELATED ANALOGS

[75] Inventor: Elie Abushanab, Peacedale, R.I.

[73] Assignee: Cypros Pharmaceutical Corporation, Carlsbad, Calif.

[21] Appl. No.: 308,590

[22] Filed: Sep. 19, 1994

Related U.S. Application Data

[63] Continuation-in-part of Ser. No. 4,721, Jan. 14, 1993, abandoned.

[51] Int. Cl.$^6$ ............. A61K 31/52; C07D 473/18; C07D 473/32; C07D 473/34
[52] U.S. Cl. ............. 514/261; 514/262; 514/263; 544/244; 544/263; 544/264; 544/265; 544/277
[58] Field of Search ................. 544/264, 277, 544/244, 265, 267; 514/261, 262, 263

[56] References Cited

U.S. PATENT DOCUMENTS 5,284,837  2/1994  Lindborg et al. ............. 514/81

OTHER PUBLICATIONS

Abushanab, E., et al, "Practical Enantiospecific Synthesis of (+)-erythro-9-(2-Hydroxy-3-nonyl)adenine," *Tetrahedron Lett.* 25: 3841 (1984).
Harriman, G. C. B., et al, "Adenosine Deaminase Inhibitors: Synthesis and Biological Evaluation of C1' and Nor-C1' Derivatives of (+)-erythro-9-(2(S)-Hydroxy-3(R)-nonyl)adenine," *J. Med. Chem.* 35: 4180–4184 (1992).
Bastian, G., et al, "Adenosine Deaminase Inhibitors: Conversion of a Single Chiral Synthon into erythro- and threo-9-(2-hydroxy-3-nonyl)adenines," *J. Med. Chem.* 24:1383–1385 (1981).
Baker, D. C., and Hawkins, L. D., "Synthesis of Inhibitors of Adenosine Deaminase: A Total Synthesis of erythro-3-(Adenin-9-yl)-2-nonanol and Its Isomers from Chiral Precursors," *J. Org. Chem.* 47: 2179–2184 (1982).
Cristalli, G., et al, "Adenosine Deaminase Inhibitors: Synthesis and Biological Activity of Deaza Analogues of erythro-9-(2-Hydroxy-3-nonyl)adenine," *J. Med. Chem.* 31: 390–397 (1988).
Cristalli, G., et al, "Adenosine Deaminase Inhibitors: Synthesis and Structure–Activity Relationships of Imidazole Analogues of erythro-9-(2-Hydroxy-3-nonyl)adenine," *J. Med. Chem.* 34: 1187–1192 (1991).
Abushanab, E., "L–ascorbic and D–isoascorbic acids: chiron sources for 1',2'–seco–nucleosides/tides, phosphonates, and other molecules of biological interest," pp. 159–175 in *Nucleosides and Nucleotides as Antitumor and Antiviral Agents,* C. K. Chu and D. C. Baker, eds. (Plenum Press, New York, 1993).
Abushanab et al I, Tetrahedron Letters, vol. 25, No. 35, pp. 3841–3844 (1984).
Abushanab et al II, J. Org. Chem., vol. 53, pp. 2598–2602 (1988).
Antonini et al, J. Med. Chem., vol. 27, pp. 274–278 (1984).
Baker et al, J. Org. Chem., vol. 47, pp. 2179–2184 (1982).
Bastian et al, J. Med. Chem., vol. 24, pp. 1383–1385 (1981).
Cristalli et al, J. Med. Chem., vol. 31, pp. 390–393 (1988).
Harriman et al, J. Med. Chem., vol. 35, pp. 4180–4184 (1992).
Porter et al, Biochemistry, vol. 31, No. 35, pp. 8216–8220 (1992).

*Primary Examiner*—Floyd D. Higel
*Attorney, Agent, or Firm*—Patrick D. Kelly

[57] ABSTRACT

This invention discloses various analogs of erythro-hydroxynonyladenine (EHNA) which have been modified by the addition of hydroxy groups or other moieties at the #8 or #9 carbon atoms of the side-chain portion of the molecule (i.e., the erythro-hydroxynonyl chain which is attached to the adenosine ring structure). It also discloses synthetic reagents and steps that can be used to create these and other analogs of EHNA which contain hydroxyl, halide, acid, ester, ether, amine, azide, or other moieties at such locations, or at other controllable locations such as the #5, #6, or #7 carbon atoms on the side-chain. Analogs containing such side-chain modifications can also be modified in the adenosine structure if desired. The hydroxylated analogs described herein have been shown to inhibit adenosine deaminase (ADA) at therapeutically useful levels. The relevant Ki values are in the range of $10^{-8}$ to $10^{-9}$, which is within a desired range of about $10^{-7}$ to about $10^{-10}$. EHNA analogs that have potencies within this range can effectively inhibit ADA activity on a reversible basis, without permanently poisoning the enzyme. It has also been discovered that some of these analogs have an additional therapeutic value when used to protect heart muscle against ischemic damage.

13 Claims, 4 Drawing Sheets

| COMPOUND | R | R' | |
|---|---|---|---|
| [9] | CH₂OH, | Bn | |
| [24] | CH₂OBz | Bn | } a |
| [25] | CH₂OBz | H | } b  } c |
| [26] | CH₂N-phtha | Bn |  } d |
| [27] | CH₂N-phtha | H | } b  } e |
| [28] | CH₂Cl | Bn | |
| [29] | CH₂Cl | H | } b |
| [30] | COOCH₃ | Bn | |
| [31] | COOCH₃ | H | } b |
| [7] | =CH₂ | Bn | } f |
| [32] | =CH₂ | H | |

REACTIONS a = BzOH, PPh₃, DIAD, THF
b = Pd(OH)₂/C, cyclohexene, ethanol
c = Phthalimide, PPh₃, DIAD, THF
d = CCl₄, NaHCO₃, PPh₃
e = PDC & DMF, then MeOH & H₂SO₄
f = NaNH₂, toluene

HYDROXYLATED ERYTHRO-HYDROXYNONYLADENINES AND RELATED ANALOGS

RELATED APPLICATION

This application is a continuation-in-part of U.S. application Ser. No. 08/004,721, filed on Jan. 14, 1993, now abandoned.

BACKGROUND OF THE INVENTION

This invention is in the fields of chemistry and pharmacology, and relates to drugs that can inhibit adenosine deaminase. Such drugs can be used to reduce the metabolic degradation of chemotherapeutic and anti-viral drugs.

The compound erythro-hydroxynonyladenine (EHNA, which is usually pronounced as "eenah") is known to inhibit the activity of an enzyme called adenosine deaminase (ADA, also known as adenosine aminohydrolase). ADA, which is designated E.C.3.5.4.4 under the international classification system, converts adenosine into inosine by removing an amine group which is attached to the #6 carbon in the two-ring adenyl structure of adenosine.

ADA can also degrade a number of other molecules, including several nucleoside analogs that are used in cancer chemotherapy or for anti-viral therapy. Therefore, ADA inhibitors can be used as adjuncts (i.e., as secondary agents to increase the effectiveness of a primary drug) to prolong the metabolic half-lives of therapeutic drugs during cancer or anti-viral chemotherapy. ADA inhibitors can also be used to artificially create ADA deficiencies, which are of interest to researchers.

EHNA, a relatively mild ADA inhibitor, is a stereoisomer with the following chemical structure, which shows the numbering of the carbon atoms in the side chain (i.e., in the erythro-hydroxynonyl structure that is attached to the adenyl group):

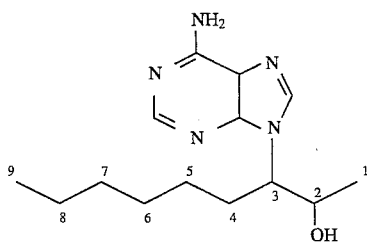

The "erythro-" prefix indicates a certain stereoisomeric arrangement of the atoms attached to the #2 and #3 carbon atoms, which are both chiral atoms. Other isomers having a different stereoisomeric arrangement are often referred to as "threo-" compounds. A racemic mixture (i.e., a mixture containing both D (+) and L isomers) containing EHNA was identified as an ADA inhibitor in Schaeffer and Schwender 1974. Subsequent reports, including Bastian et al 1981 and Baker and Hawkins 1982, identified the (+)-2S,3R isomer as the most potent ADA inhibitor from among the various hydroxynonyladenine isomers.

Various analogs and derivatives of EHNA have been described in reports such as Harriman et al 1992. Those other analogs are not related to the EHNA analogs described herein.

EHNA apparently is metabolized and cleared from the mammalian bloodstream fairly rapidly (McConnell et al 1980; Lambe and Nelson 1982). In addition, ADA inhibition by EHNA is not as strong as certain other known compounds, including deoxycoformycin (dCF, also known as Pentostatin). The Ki value of dCF (i.e., the concentration of dCF required to inactivate a standardized quantity of ADA) is very low, about $2.5 \times 10^{-12}$ which indicates that dCF binds to ADA very tightly; dCF is sometimes called a "suicide inhibitor," which indicates that the binding between dCF and ADA is effectively irreversible and neither molecule can be regenerated. Because of its potency as an ADA inhibitor, dCF has been tested by several research teams to determine whether it can be used therapeutically. Although dCF reportedly provided some beneficial activity in cardiovascular models (e.g., Dorheim et al 1991) and in neuroprotective models (e.g., Phillis and O'Regan 1989), it was found to cause serious and unpredictable toxic side effects in some animals. Therefore, attention has returned to EHNA as a milder or "softer" ADA inhibitor with fewer side effects. The Ki value of EHNA is about $4 \times 10^{-9}$, which indicates that EHNA binds to ADA about a thousand times less tightly than dCF.

One object of this invention is to disclose a class of hydroxylated derivatives of EHNA which can inhibit ADA activity at therapeutically effective levels without irreversibly inactivating (poisoning) the ADA enzyme.

Another object of this invention is to disclose synthetic reagents and methods that can be used to create analogs of EHNA which contain hydroxyl, halide, acid, ester, ether, amine, azide, or other moieties at various controllable locations in the side chain.

Another object of this invention is to disclose a new set of EHNA analogs which can be used to slow down the degradation of certain types of useful therapeutic drugs by ADA.

SUMMARY OF THE INVENTION

This invention discloses various analogs of erythro-hydroxynonyladenine (EHNA) which have been modified by the addition of hydroxy groups or other moieties at the #8 or #9 carbon atoms of the side-chain portion of the molecule (i.e., the erythro-hydroxynonyl chain which is attached to the adenosine ring structure). It also discloses synthetic reagents and steps that can be used to create these and other analogs of EHNA which contain hydroxyl, halide, acid, ester, ether, amine, azide, or other moieties at such locations, or at other controllable locations such as the #5, #6, or #7 carbon atoms on the side-chain. Analogs containing such side-chain modifications can also be modified in the adenosine structure if desired. The hydroxylated analogs described herein have been shown to inhibit adenosine deaminase (ADA) at therapeutically useful levels. The relevant Ki values are in the range of $10^{-8}$ to $10^{-9}$, which is within a desired range of about $10^{-7}$ to about $10^{-10}$. EHNA analogs that have potencies within this range can effectively inhibit ADA activity on a reversible basis, without permanently poisoning the enzyme. It has also been discovered that some of these analogs have an additional therapeutic value when used to protect heart muscle against ischemic damage.

DESCRIPTION OF THE PREFERRED EMBODIMENTS

This invention describes analogs of EHNA in which the side chain (i.e., the erythro-hydroxynonyl portion, which is attached to an adenyl structure) has been chemically modified by addition of a hydroxyl or other group. Useful analogs within this class include EHNA analogs that are pharmacologically acceptable inhibitors of adenosine deaminase, as discussed below.

This invention also discloses a method of synthesizing analogs of EHNA in which a hydroxyl or other moiety has been added to the side chain. This method comprises the following steps:

a. reacting an epoxide reagent having a desired chiral orientation with an alkyl halide reagent having an unsaturated bond between two selected carbon atoms, under conditions which cause said reagents to create an unsaturated aliphatic compound comprising a first portion having a desired chiral orientation and a second portion having an unsaturated bond;

b. reacting the unsaturated aliphatic compound with at least one third reagent, under conditions which cause the third reagent to modify the unsaturated aliphatic compound by adding at least one hydroxyl group to at least one of the carbon atoms involved in the unsaturated bond, thereby creating a hydroxylated saturated aliphatic compound.

When these basic steps have been completed, any additional processing is carried out which is necessary to complete the synthesis of the desired hydroxylated analog, and the analog is then purified. The particular processing and purification steps used to create a specific analog will depend on the exact molecular structure of the desired analog. Such steps are within the ordinary skill in the art, and various examples of suitable reagents and reactions which can be used for such purposes are described below.

Example 1, below, sets forth in detail the reagents and reactions used to synthesize a number of hydroxylated or halogenated EHNA analogs. The epoxide starting reagent, intermediate compounds generated during the multi-step synthesis, and the final EHNA analogs are identified by the full chemical names in the subheadings under Example 1, and by bracketed numbers that are used for convenience in the Examples and in FIGS. 1 and 2.

Figure 1:
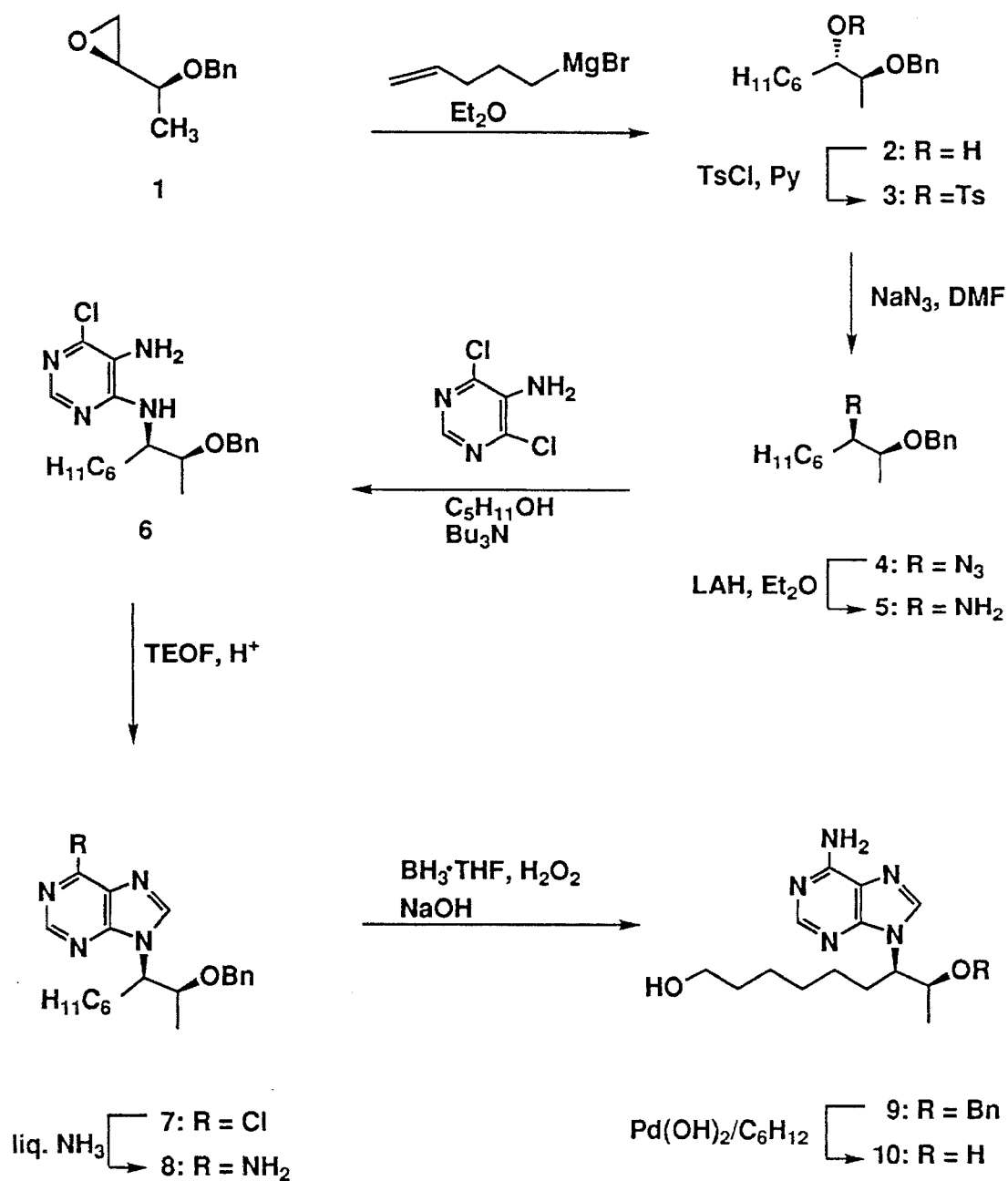
FIG. 1 depicts a series of chemical reactions used to create 9'-hydroxy(+)-EHNA, designated as Compound [10].

One of the hydroxylated EHNA analogs which was shown to inhibit ADA activity is Compound [10]. Its full chemical name is 9-[2(S),9-dihydroxy-3(R)-nonyl]adenine, and it is also referred to herein as 9-hydroxy-EHNA, or as 9-OH-EHNA. Its synthesis is depicted in FIG. 1.

Figure 2:
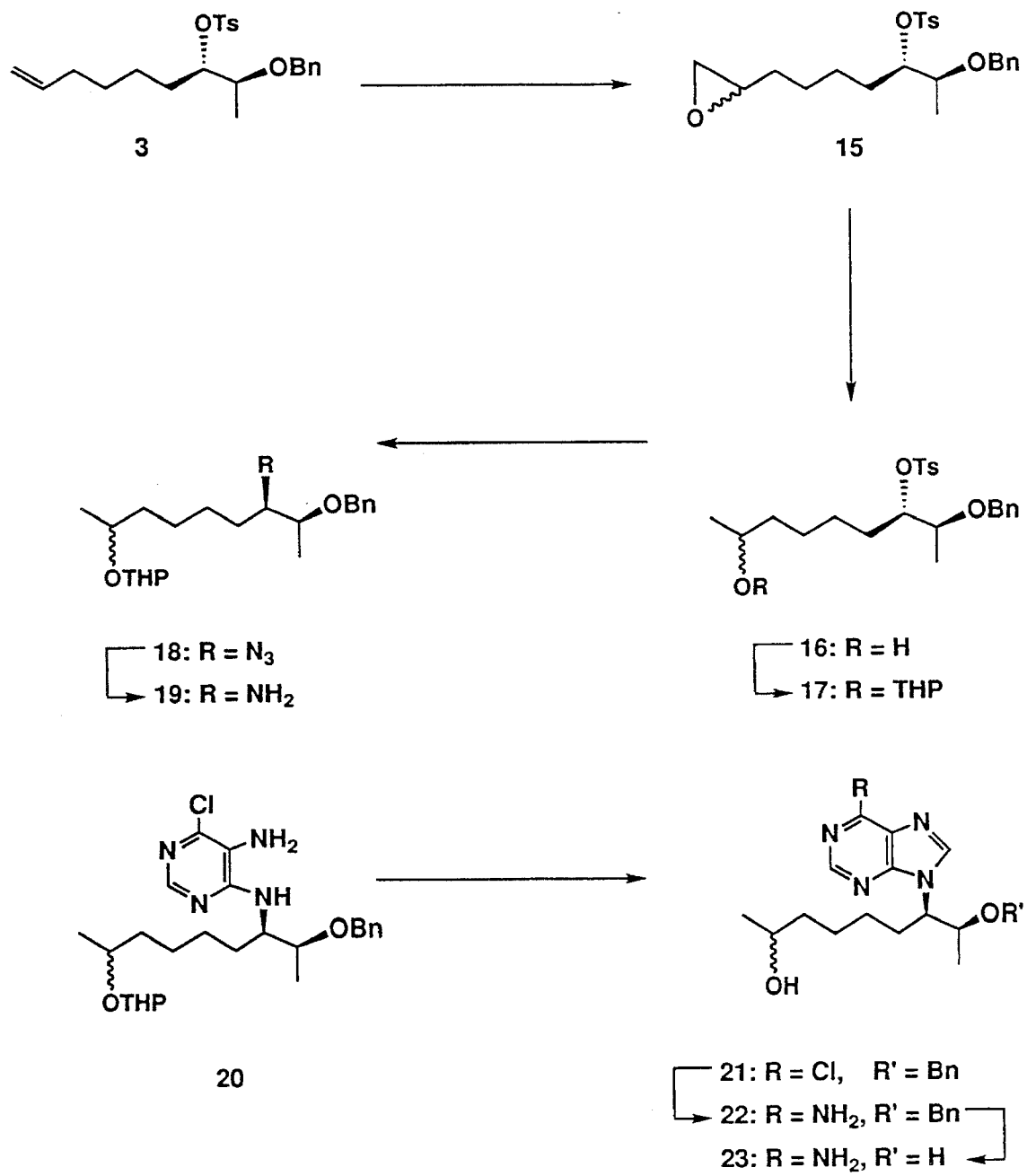
FIG. 2 depicts the reactions used to create 8'-hydroxy(+)-EHNA, designated as Compound [23].

Another hydroxylated EHNA analog which inhibits ADA activity is Compound [23]. Its full chemical name is 9-[2(S), 8-dihydroxy- 3(R)-nonyl]adenine; it is also referred to as 8-hydroxy-EHNA, or as 8-OH-EHNA. Its synthesis is depicted in FIG. 2.

Figure 3:
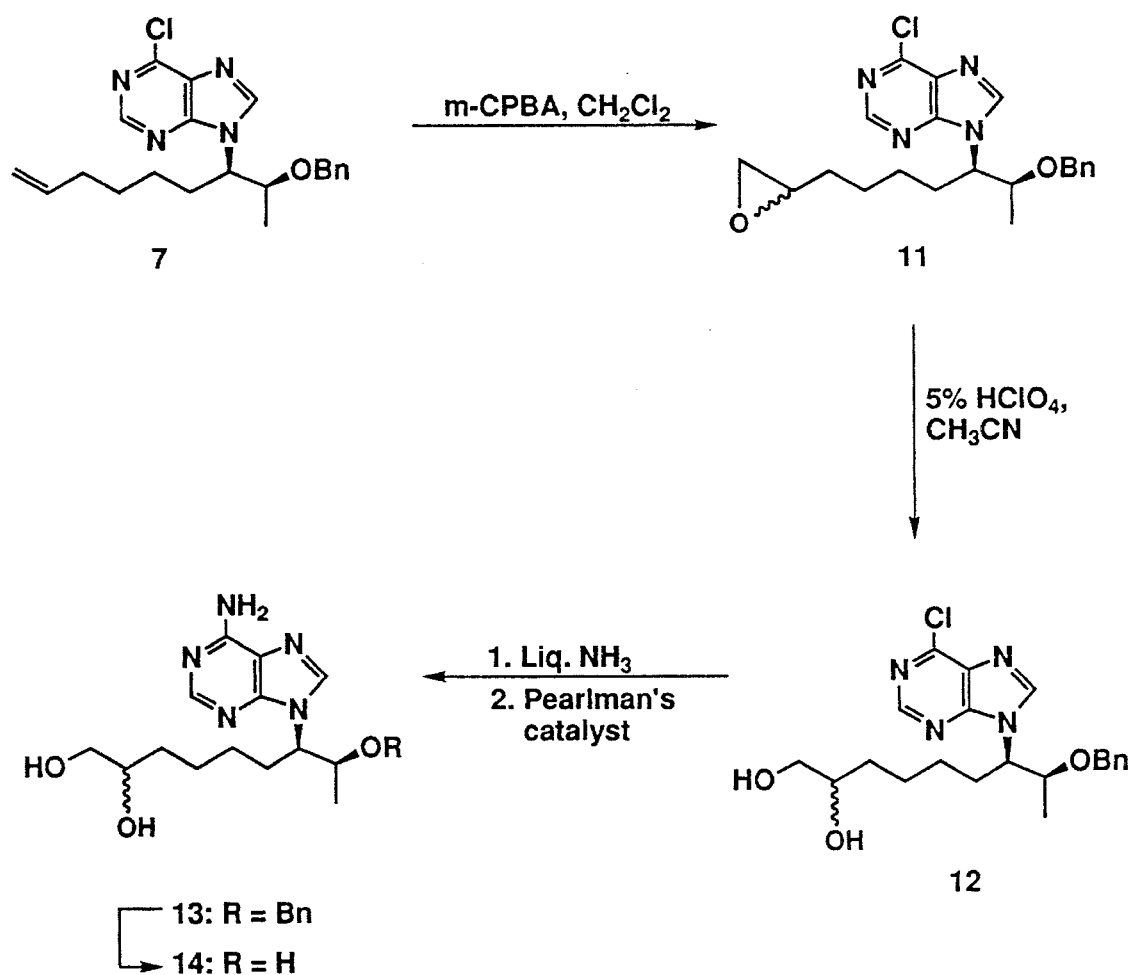
FIG. 3 depicts the reactions used to create 8', 9'-dihydroxy(+)-EHNA, designated as Compound [14].

Compound [14] is a dihydroxylated EHNA analog with hydroxy groups added to both the 8' and 9' carbon atoms. Its synthesis is depicted in FIG. 3. It also inhibits ADA activity.

If desired, the hydroxyl groups on the #8 or #9 carbon atoms or will allow the creation of any other analog that can be generated by substituting or derivatizing hydroxyl groups. Such derivatives include halides, carboxylic acid groups, esters, ethers, etc., all of which can be created using the techniques such as disclosed in Example 3 or other techniques known to those skilled in the art. A hydroxyl group can also be converted into an azide group, by methods such as reacting the hydroxyl with p-toluenesulfonyl chloride (TsCl) to create an O-tosyl group (abbreviated as OTs in the figures; tosyl refers to toluenesulfonyl), then reacting the O-tosyl compound with sodium azide ($NAN_3$), which displaces the O-tosyl group and leaves an $N_3$ group attached to the carbon chain.

Epoxide [1] was synthesized as described in Abushanab et al 1984 and 1988. It controls the orientation of the substituents on the two chiral carbon atoms in the final EHNA analog, which are provided by the #3 and #4 carbons in the epoxide. To synthesize different stereoisomers of any of the EHNA analogs discussed herein, different epoxide stereoisomers having any desired chiral configuration can be used as the starting reagent.

The benzyl group ($-CH_2C_6H_5$) which was attached via an oxygen atom to the #3 carbon in the starting epoxide served as a protective group for the oxygen atom. In the final step of synthesis of each of the hydroxylated EHNA analogs, the benzyl group was displaced by hydrogen to create a hydroxyl group on the #2 carbon of the side chain. That #2 hydroxyl group is part of the normal EHNA molecule. If desired, that hydroxyl group can be eliminated by using a starting epoxide without a protected oxygen atom, or it can be modified during synthesis to provide a halide, carboxylic, ester, ether, azide, or other group, as described above. If a moiety is desired at the #1 carbon atom in the final EHNA analog, it can be provided by using a starting epoxide having the desired moiety or a precursor at the #4 carbon atom of the epoxide.

The synthesis reactions described herein also offer a method of adding hydroxyl derivatives to the #4, #5, #6, or #7 carbon atoms on the side chain. Those carbon atoms were provided by the reagent 1-pentenylmagnesium bromide, which has a structure as shown in FIG. 1 in the reaction that converts epoxide [1] into compound [2]. The 1-pentenyl notation indicates that the unsaturated double bond is positioned between the #1 and #2 carbon atoms in 1-pentenylmagnesium bromide; those carbon atoms ultimately become the #8 and #9 carbon atoms in the EHNA analogs of this invention. The unsaturated carbon atoms in the double-bonded pentenyl compound become attachment points for hydroxyl groups during the reaction which converts compound [8] into compound [9]. Hydroxyl groups were added to both of the unsaturated carbons, and the compound having the hydroxyl moiety at the desired location was subsequently purified. In an alternate approach, the double bond supplied by the pentenyl compound was converted into an epoxide intermediate, as shown in FIG. 2 in the reaction which generated compound [15].

Using either of these approaches, the location of the hydroxyl group on the side chain of an EHNA analog can be controlled by using a pentenylmagnesium bromide (or similar) compound having a double bond in any desired location. A 2-pentenyl compound would have a double bond between its #2 and #3 carbon atoms, which become the #8 and #7 carbon atoms in the final EHNA analog. A 3-pentenyl reagent (having a double bond between its #3 and #4 carbon atoms) would generate hydroxyl groups attached to the #7 or #6 carbons in the EHNA analog.

FIG. 2 also depicts a halogenated analog, Compound [21]. In Compound [21], the halogen (chlorine) atom was substituted into the adenine structure. Although that chlorine atom was substituted by an amine group during the synthesis of compound [22], that particular reaction could be omitted if desired, so that the halogen moiety would remain after removal of the benzyl protective group.

The method used to create the adenyl structure in the EHNA analogs described herein offers a general method for making various changes in the adenine group. The adenyl structure was provided by supplying and then manipulating a heterocyclic compound, 5-amino-4,5-dichloropyrimidine (ADCP), which is shown in FIG. 1 in the reaction that generated compound [6]; this same reagent was also used to generate compound [20] shown in FIG. 2. The ADCP was coupled to the side chain by displacing one of the chlorine atoms on the ADCP with an amine group that was coupled to the side chain. The five-member ring in the adenine structure was then closed by forming a carbon bond between two proximal nitrogen atoms.

If desired, alternate heterocyclic reagents could be used instead of ADCP, to create analogs of EHNA with modified adenine structures, either as moieties attached to one of the rings, or as differing atoms incorporated into either of the rings. Cristalli et al 1988 and 1991 report that certain analogues of EHNA with modified adenine structures (such as a 3-deaza-EHNA derivative) are active as ADA inhibitors. Such modifications to the adenyl structure could be incorporated into the analogs of this invention, which have modified side chains.

All the hydroxylated EHNA analogs which were tested for ADA inhibition (as described in Example 2) were shown to be active. The 9-hydroxy analog (compound [10]) was the strongest binding agent of the three, with a Ki value of $3.4 \times 10^{-9}$; the 8-hydroxy-EHNA analog (compound [23]) was the weakest, with a Ki value of $11 \times 10^{-9}$. The 8,9-dihydroxy analog (compound 14]) had an intermediate strength, with a Ki value of $6 \times 10^{-9}$.

All three of these Ki values are within a desired range, which covers about $10^{-7}$ to about $10^{-10}$. At one end of the desired range, ADA inhibitors having Ki values lower than about $10^{-10}$ run the risk of "poisoning" the enzyme by binding to it so tightly that the reaction is, for all practical purposes, irreversible. At the other end of the desired range, ADA inhibitors having Ki values higher than about $10^{-7}$ tend to be insufficiently potent to accomplish the desired level of ADA inhibition; they would need to be administered in relatively large quantities, and even in large quantities they might not be adequately potent.

The EHNA analogs described herein can be administered as adjuncts to prolong the half-lives and increase the effectiveness of chemotherapeutic drugs (usually used as anti-cancer or anti-viral agents) that are degraded by ADA. As will be recognized by those skilled in the art, the desired range of Ki values is relatively broad, since candidate compounds can be administered to a patient at any desired level, by various routes. An analog having a Ki value in the range of about $10^{-9}$ should be administered in relatively low dosages, such as up to about 10 milligrams per kilogram of body weight per day if injected intravenously, and up to about 50 mg/kg/day if administered orally. A less potent analog having a Ki value in the range of about $10^{-7}$ could be administered in higher dosages, such as up to about 25 mg/kg/day if administered orally or injected in response to a major crisis, or up to 20 mg/kg/day if injected intravenously. Since the metabolic problems caused by ADA deficiency tend to accumulate slowly, short-term dosages can be rather large.

In addition, the hydroxylated EHNA analogs described herein were tested for protection against tissue damage caused by ischemia (lack of adequate blood flow, which occurs during various events such as heart attack, cardiac arrest, and stroke). In tests involving hearts removed from lab animals, 9-OH-EHNA provided a significantly higher level of protection against an important form of muscle damage, compared to unmodified EHNA. These results and the test procedures are described in Example 5. This useful biological activity could not have been predicted prior to the experiments, and it helps overcome any presumption of obviousness of hydroxylated analogs based upon prior art concerning EHNA.

Included within the family of agents useful for the purposes described herein are any isomers (including "threo" isomers), analogs, or salts of the compounds described herein, provided that such isomers, analogs, and salts are functionally effective as ADA inhibitors, and are pharmacologically acceptable. The term "pharmacologically acceptable" embraces those characteristics which make a drug suitable and practical for administration to humans; such compounds must be sufficiently chemically stable to have an adequate shelf life under reasonable storage conditions, and they must be physiologically acceptable when introduced into the body by a suitable route of administration. Acceptable salts can include alkali metal salts as well as addition salts of free acids or free bases. Examples of acids which are widely used to form pharmacologically acceptable acid-addition salts include inorganic acids such as hydrochloric acid, sulfuric acid and phosphoric acid, and organic acids such as maleic acid, succinic acid and citric acid. Alkali metal salts or alkaline earth metal salts could include, for example, sodium, potassium, calcium or magnesium salts. All of these salts may be prepared by conventional means. The nature of the salt is not critical, provided that it is non-toxic and does not substantially interfere with the desired activity. The potency of any candidate isomer, analog, or salt in inhibiting ADA activity can be tested using methods such as described in Example 2.

The term "analog" is used herein in the conventional pharmaceutical sense. In chemical terminology, an analog refers to a molecule that structurally resembles a referent molecule but which has been modified in a targeted and controlled manner to replace a certain substituent of the referent molecule with an alternate substituent other than hydrogen. Such analogs are covered by the claims herein only if they satisfy the efficacy requirements disclosed herein, in a manner which does not destroy the desired function of ADA inhibition by the compound at a Ki value in the range of about about $10^{-7}$ to about $10^{-10}$ and which does not render the analog pharmacologically unacceptable. By way of example, the hydroxylated compounds [10], [14], and [23] are all analogs of EHNA; by contrast, the standard form of EHNA is not regarded as an analog of 9-hydroxy-EHNA. Any coverage of claims which refer to additional analogs derived from the hydroxylated analogs disclosed herein is limited to analogs which are pharmacologically acceptable and which exhibit a suitable and desirable level of activity in inhibiting ADA.

Administration of the compounds of this invention to humans or animals can be by any technique capable of introducing the compounds into the bloodstream, including oral administration or via intravenous or intramuscular injections. The active compound is usually administered in a pharmaceutical formulation such as in a liquid carrier for injection, or in capsule, tablet, or liquid form for oral ingestion. Such formulations may comprise a mixture of one or more active compounds mixed with one or more pharmaceutically acceptable carriers or diluents. If desired, other therapeutic agents (such as anti-cancer or anti-viral nucleoside analogs) may also be present in an injectable formulation or an ingestible capsule, tablet, or liquid.

EXAMPLES

EXAMPLE 1

Synthesis of Compounds

This example describes how various intermediate and final compounds were synthesized. For convenience, bracketed numbers which correspond to the subheadings below and to the call-out numbers in the drawings are used to refer to each compound.

Melting points were determined on a Buchi 535 melting point apparatus and are uncorrected. The $^1$H NMR spectra were recorded on a Varian EM-390 or a Bruker AM-300 spectrometer. The chemical shifts are expressed in parts per million with respect to tetramethylsilane. Optical rotations were obtained with a Perkin Elmer Model 141 digital readout polarimeter. Unless otherwise indicated, all organic solutions were dried over anhydrous sodium sulfate, filtered, and evaporated to dryness under reduced pressure. Ratios of chromatography solvents are expressed in v/v. Silica gel (Davison, grade H, 230–425 mesh) suitable for flash column chromatography was purchased from Fisher Scientific. A Chromatotron (centrifugally accelerated, preparative thin-layer, radial chromatograph) Model 7924T was used to complete various separations. The 1.0 and 2.0 mm plates used were coated with silica gel PF254 containing $CaSO_4$. Elemental analyses were performed by MHW Laboratories (Phoenix, Ariz.).

COMPOUND 1

(2S,3S)-3-(benzyloxy)-1,2-epoxybutane

The starting epoxide [1] was synthesized as described in Abushanab et al 1984 and 1988. This epoxide determines the orientation of the substituents on the two chiral carbon atoms in the final EHNA analog, which are provided by the #3 and #4 carbons in the epoxide. To synthesize different stereoisomers of any of the EHNA analogs discussed herein, different epoxide stereoisomers having any desired chiral configuration can be used as the starting reagent. A benzyl group attached to the #3 carbon atom via an oxygen atom was used to protect the oxygen atom during synthesis.

COMPOUND 2

(2S, 3S) -2-O-Benzyl-2,3-non-8-en-diol

A solution of epoxide [1] (2g, 11.24 mmol) in ether (50 mL) was added to a cold (−78° C.) ether solution containing 1-pentenylmagnesium bromide [ (22.5 mmol), prepared by reacting magnesium (0.66 g, 22.5 mmol) and 5-bromopentene (4.11 g, 22.5 mmol) ] and 0.1 mmol of lithium tetrachlorocuprate, while stirring was continued for 1 h. The reaction was quenched with a saturated solution of $NH_4Cl$ (100 mL) and extracted with ether. Pure [2] (2.67 g, 96%) was obtained by silica gel column chromatography eluting with a mixture of ethyl acetate (EtOAc) and hexane (5:95): [alpha]$D^{25}$+ 2.09 (c, 1.65, EtOH); $^1$H NMR (CDCl$_3$) delta 1.13 (d, J= 6 Hz, 3H), 1.13–1.28 (m,6H), 1.81–2.28 (m,2H), 2.45– 2.68 (bs, $^1$H, $D_2O$ exchangeable), 3.05–3.65 (m,2H), 4.25–4.75 ($q_{AB}$, J= 12 Hz, 2H), 4.75–5.05 (m,2H), 5.45–5.98 (m,1H), 7.25 (s,5H).

Calculated values for $C_{16}H_{24}O_2$: C, 77.41; H, 9.67. Found: C, 77.25; H. 9.82.

COMPOUND 3

(2S, 3S) -2-O-Benzyl-3-O-tosyl-2,3-nona-8-en-diol

To a stirred solution of the alcohol [2] (5.4 g, 21.7 mmol) in pyridine (10 mL) was added p-toluenesulfonyl chloride (TsCl; 4.5 g, 23.9 mmol) and stirring was continued for 12 h at room temperature (RT). The mixture was poured into water (100 mL) and extracted with $CH_2Cl_2$ (3×100 mL). The combined organic solutions were then washed with cold HCl (2×50 mL) and water (2× 100 mL), dried (MgSO$_4$) and filtered. Removal of solvent left an oil, which was purified by silica gel chromatography eluting with EtOAc-hexane (1:50) to afford [3] (8.35 g, 97%): [alpha]$D^{25}$+ 11.46 (c, 2.62, EtOH); $^1$H NMR (CDCl$_3$) delta 1.13 (d, J= 6 Hz, 3H), 1.13–2.1 (m,8H), 2.43 (s,3H), 3.5–3.83 (m, 1H), 4.23–4.63 ($q_{AB}$, J= 9 Hz, 2H), 4.46–4.66 (m, $^1$H), 4.76–5.03 (m, 2H), 5.4–5.93 (m, 1H), 7.18 (d, J= 7.5 Hz, 2H), 7.23 (s,5H), 7.73 (d, J= 7.5 Hz, 2H) .

Calculated values for $C_{23}H_{30}O_4S$: C, 68.65; H, 7.4 6; S, 7.96. Found: C, 68.69; H. 7.40, S, 8.13.

COMPOUND 4

(2S,3R)-3-Azido-2-O-benzyl-2-nona-8-en-ol

Sodium azide (1.027 g, 15.8 mmol) was added to a stirred solution of [ 2 ] ( 4.0 g, 13.2 mmol) in anhydrous DMF ( 20 mL) . After refluxing for 45 min, DMF was removed and pure [4] (2.61 g, 96%) was obtained by silica gel column chromatography eluting with EtOAc-hexanes (5:95); [alpha]$D^{25}$+12.45 (c, 2.5, EtOH); $^1$H NMR (CDCl$_3$) delta 1.2(d, J= 6 Hz,3H), 1.3–1.8 (m,6H), 1.9–2.23 (m,2H), 3.24–3.7 (m,2H), 4.5 ($q_{AB}$, J=7.5 Hz, 2H), 4.76–5.13 (m,2H), 5.46–6.03 (m, 1H), 7.23 (s,5H).

Calculated values for $C_{16}H_{23}ON_3$: C, 70.32; H, 8.42; N, 15.38. Found: C, 70.28; H. 8.66, N, 15.18.

COMPOUND 5

(2S, 3R) -3-Amino-2-O-Benzyl-2-nona-8-en-01

To a stirred solution of lithium aluminum hydride (LAH, 0.25 g, 5.2 mmol) in anhydrous ether (50 mL) was added, dropwise, a solution of azide [4] (1 g, 3.66 mmol) in anhydrous ether (50 mL). The reaction mixture was then heated at reflux for 2 h, cooled to RT, and excess LAH was decomposed by the careful successive dropwise addition of water (0.25 mL), 15% NAOH (0.24 mL), and water (0.5 mL). Filtration, drying and evaporation of the solvent gave a pure colorless liquid [5] (1.06 g, 96%). [alpha]$D^{25}$+17.66 (c, 5.37, EtOH); $^1$H NMR (CDCl$_3$) delta 1.3 (d, J= 6 Hz, 3H) , 0.96–1.66 (m, 8H, 2D$_2$O exchangeable) , 1.86–2.26 (m,2H), 2.76–3.03 (m, 1H), 3.23–3.56 (m, 1H), 4.5 ($q_{AB}$ J=7.5 Hz, 2H), 4.76–5.1 (m,2H), 5.5–6.03 (m, 1H), 7.26 (s,5H).

Calculated values for $C_{16}H_{25}ON$: C, 77.73; H, 10.12; N, 5.66. Found: C, 77.70; H, 10.31; N, 5.34.

COMPOUND 6

5-Amino-6-chloro-4[2(S)-O-benzyl-3(R)-nona-8-enyl]aminopyrimidine

5-Amino-4,5-dichloropyrimidine (ADCP, 0.39 g, 2.336 mmol), N-tributylamine (n-Bu$_3$N; 0.433 g, 2.336 mmol) and [5] (0.5907 g, 2.336 mmol) in anhydrous pentanol (10 mL) was heated at reflux for 48 h under an N$_2$ atmosphere. Pentanol and n-Bu$_3$N were removed and the residue was chromatographed over silica gel (EtOAc-hexanes 1:10) to give [6] (0.65 g, 74%); [alpha]D$^{25}$+38.4 (c, 1.775, EtOH); $^1$H NMR (CDCl$_3$) delta 1.2 (d, J= 6 Hz, 3H), 1.1–2.23 (m,8H), 3.3–3.9 (m,3H, 2D$_2$O exchangeable), 4.43 (q$_{AB}$,J= 13.5, 2H), 4.00–4.40 (bs, 1H, D$_2$O exchangeable), 4.66–5.36 (m, 3H), 5.40–5.96 (m, 1H), 7.23 (s,5H), 7.90 (s,1H).

Calculated values for C$_{20}$H$_{27}$ON$_4$Cl: C, 64.08; H, 7.21; N, 14.95; Cl, 9.47. Found: C, 64.24; H, 7.17; N, 14.83; Cl, 9.31.

COMPOUND 7

6-Chloro-9-[2(S)-O-benzyl-3(R)-nona-8-en-enyl]purine

An acidified (conc. HCl 0.3 mL) solution of [6] (0.58 g, 1.55 mmol) in triethyl orthoformate (TEOF; 15 mL) was stirred at RT for 24 h. The yellow oil obtained after removal of TEOF, was purified by silica gel column chromatography eluting With EtOAc-hexanes (1:10) to provide [7] (0.5 g, 85%); [alpha]D$^{25}$+54.49 (c 3.74, EtOH); $^1$H NMR (CDCl$_3$) delta 1.26 (d, J 6 Hz, 3H), 0.73–1.60 (m, 4H), 1.60–2.40 (m, 4H), 3.53–4.00 (m, $^1$H), 4.4 (q$_{AB}$ J 13.5 Hz, 2H), 4.5–5.03 (m,3H), 5.33–5.9 (m, 1H), 7.13 (s,5H), 8.23 (s,1H), 8.63 (s,1H).

Calculated values for C$_{21}$H$_{25}$ON$_4$Cl: C, 65.53; H, 6.50; N, 14.56; Cl, 9.23. Found: C, 65.42; H, 6.46; N, 14.49; Cl, 9.37.

COMPOUND 8

9-[2(S)-O-Benzyl-3(R)-nona-8-enyl]adenine

Compound [7] (0.3 g, 0.78 retool) was dissolved in liquid ammonia (15 mL) and heated at 90° C. in a steel bomb for 24 h. After cooling, excess ammonia was allowed to evaporate. The residue was taken up in CH$_2$Cl$_2$ (25 mL) and washed with water (10 mL). The organic layer was dried and pure [8] (0.245 g, 85%) was obtained as a white solid: [alpha]D$^{25}$+68.01 (c, 1.375, EtOH); $^1$H NMR (CDCl$_3$) delta 1.20 (d, J= 6 Hz, 3H), 0.65–1.60 (m,4H), 1.66– 2.26 (m,4H), 3.56–4.00 (m, 1H), 4.4 (q$_{AB}$,J=6 Hz, 2H), 4.43–5.03 (m,3H), 5.33–5.93 (m, 1H), 6.03–6.40 (bs, 2H, D$_2$O exchangeable), 7.16 (s,5H), 7.9 (s,1H), 8.26 (s,1H).

Calculated values for C$_{21}$H$_{27}$ON$_5$: C, 69.04; H, 7.39; N, 19.17. Found: C, 69.17; H, 7.39; N, 19.20.

COMPOUND 9

9-[2(S)-O-Benzyl-9-hydroxy-3(R)-nonyl]adenine

To a solution of the olefin [8] (0.365 g, 1 mmol) in dry tetrahydrofuran (THF; 1 mL), placed in a three-necked flask fitted with a condenser and a septum, was added a 1 M solution of a diborane-THF complex (BH$_3$.THF; 0.5 mL, 0.5 mmol) at 0° C. The reaction was done under nitrogen atmosphere. The mixture was permitted to stir for additional hours at RT to continue the completion of the reaction. Water (0.05 mL) was added slowly and the mixture was allowed to stir at RT until hydrogen no longer evolved. The flask was immersed in an ice bath and 3 molar NaOH (0.17 mL) was rapidly added to the reaction mixture. The organoboronic acid intermediate was oxidized by the slow addition of 30% hydrogen peroxide (0.11 mL). The reaction mixture was then allowed to stir for 3 h at 50° C. to ensure completion of the oxidation. The mixture was brought to RT and NaCl was added to saturate the lower aqueous phase. The THF phase was separated and dried (MgSO$_4$). The crude compound obtained after solvent removal was purified by silica gel column chromatography eluting with EtOAc to provide 9 (0.268 g, 70%): [alpha]D$^{25}$+59.04(c, 0.965, EtOH); $^1$H NMR (CDCl$_3$) delta 0.76–1.80 (m, 11H), 1.8–2.36 (m,2H), 3.30–4.80 (m, 7H, 1D$_2$O exchangeable), 6.26 (bs, 2H, D$_2$O exchangeable), 7.30 (s,5H), 7.86 (s,1H), 8.26 (s,1H).

Calculated values for C$_{21}$H$_{29}$O$_2$N$_5$: C, 65.79; H, 7.59; N, 18.27. Found: C, 65.81; H, 7.49; N, 17.99.

COMPOUND 10

9-[2[(S),9-dihydroxy-3(R)-nonyl]adenine

In order to remove the benzyl protective group, a solution of compound [9] (0.227 g, 0.593 mmol) in EtOH (25 mL) and cyclohexene (10 mL) was treated with 20% palladium hydroxide on charcoal [Pd(OH)$_2$/C, often referred to as Pearlmann's reagent, 0.05 g]. The resulting suspension was stirred at reflux for 12 h. After cooling to RT, the mixture was filtered and the filtrate was concentrated at reduced pressure. The residue was chromatographed over silica gel (EtOAc-MeOH, 9:1) to give pure [10] (0.156 g, 90%): [alpha]D$^{25}$+32.2 (c, 0,145, EtOH); $^1$H NMR (D$_2$O); 0.79–1.22 (m, 11H), 1.77–1.89 (m,2H), 3.26–3.31 (m,2H), 3.93–4.01 (m, 1H), 4.22–4.29 (m, 1H), 8.04 (s,1H), 8.06 (s,1H).

Calculated values for C$_{14}$H$_{23}$O$_2$N$_5$: C, 57.32; H, 7.90; N, 23.87. Found: C, 57.06; H, 8.03; N, 23.56.

This compound is the 9-hydroxy analog of EHNA which was tested as described in Example 2 and shown to be an effective inhibitor of ADA activity.

COMPOUND 11

6-Chloro-9-[2(S)-O-benzyl-8,9-epoxy-3(R)-nona-8-enyl]purine

To an ice cold solution of the olefin [7] (0,769 g, 2 mmol) in CH$_2$Cl$_2$ (15 mL) was added 85% m-chloroperbenzoic acid (0.488 g, 2.4 mmol). After stirring the reaction mixture at RT overnight, it was diluted with ether (50 mL) and washed successively with saturated NaHCO$_3$ (15 mL), 10% NaHSO$_3$ (15 mL), saturated NaHCO$_3$ (15 mL), and brine and dried (MgSO$_4$). The residue, obtained after evaporation of ether, was purified by silica gel column chromatography eluting with EtOAc-hexanes (1:10) to afford pure epoxide [11] (0.721 g, 90%): $^1$H NMR (CDCl$_3$) delta 1.30 (d,J= 6 Hz, 3H), 0.76–1.76 (m,6H), 1.83–2.5 (m,3H), 2.56–2.96 (m,2H), 3.66– 4.06 (m, 1H), 4.63 (q$_{AB}$ J=13.5 Hz, 2H), 4.63–4.86 (m, 1H), 7.19 (s,5H), 8.26 (s,1H), 8.66 (s,1H).

Calculated values for C$_{21}$H$_{25}$N$_4$O$_2$Cl: C, 62.91; H, 6.29; N, 13.97; Cl, 8.84. Found: C, 62.83; H, 6.41; N, 13.87; Cl, 8.74.

COMPOUND 12

6-Chloro-9[2(S)-O-benzyl-8,9-dihydroxy-3(R)-nonyl]purine

Compound [11] (0.3 g, 0.75 mmol), 5% $HClO_4$ (2 mL), in acetonitrile (6 mL) was stirred at RT for 2 h. The reaction mixture was neutralized with solid $NaHCO_3$ and the mixture was filtered. The filtrate was diluted with $CH_2Cl_2$ (25 mL) and dried over $MgSO_4$. The residue obtained after solvent evaporation was purified by silica gel column chromatography using EtOAc-hexanes (1:1) to provide diol [12] (0.3 g, 95%): $^1H$ NMR ($CDCl_3$) delta 0.70–1.66 (m, 9H), 1.66–2.43 (m, 2H), 2.5–3.96 (m, 6H, $2D_2O$ exchangeable) 4.36 ($q_{AB}$ J= 13.5 Hz, 2H), 4.4–4.7 (m, 1H), 7.12 (s,5H), 8.2 (s,1H), 8.53 (s,1H).

Calculated values for $C_{21}H_{27}O_3N_4Cl$: C, 60.21; H, 6.50; N, 13.37; Cl, 8.46. Found: C, 59.96; H, 6.58; N, 13.09; Cl, 8.53.

COMPOUND 13

9-[2(S)-O-Benzyl-8,9-dihydroxy-3(R)-nonyl]adenine

Compound [12] was obtained from [11] according to the procedure described for the preparation of [8], in 90% yield: $^1H$ NMR ($CDCl_3$) delta 0.60–1.60 (m,9H), 1.60–2.30 (m,2H), 2.93–4.86 (m,9H), 6.43 (bs, 2H, $D_2O$ exchangeable), 7.13 (s,5H), 7.83 (s,1H), 8.13 (s,1H).

Calculated values for $C_{21}H_{29}O_3N_5$: C, 63.14; H, 7.32; N, 17.53 Found: C, 63.22; H, 7.04; N, 17.27.

COMPOUND 14

9-[2(S), 8,9-trihydroxy-3(R)-nonyl]adenine

Triol [14] was prepared in 90% yield by debenzylating [13] using the procedure described for [10]. $^1H$ NMR ($D_2O$) delta 0.89–1.24 (m,9H), 1.87–1.96 (m,2H), 2.19–2.41 (m,3H), 3.98–4.02 (m, 1H), 4.28–4.33 (m, 1H), 8.08 (s,1H), 8.11 (2,1H).

Calculated values for $C_{14}H_{23}O_3N_5 \cdot 1.1$ mole $H_2O$: C, 51.08; H, 7.68; N, 21.27. Found: C, 51.10; H, 7.43; N, 20.74.

This compound is the 8,9-dihydroxy analog of EHNA which was tested as described in Example 2 and shown to be an effective inhibitor of ADA activity.

COMPOUND 15

(2S,3S)-2-O-Benzyl-3.)-O-tosyl-8,9-epoxy-2,3-nonanediol

Epoxidation of [3] was carried out as described for compound [11]. After workup, the residue was chromatographed using hexane-EtOAc (7:3) to give the epoxide [15] (99%) as an oil: $^1H$ NMR ($CDCl_3$) delta 1.06 (d, J= 6 Hz, 3H), 1.1–1.96 (m,8H), 2.36 (s,3H), 2.33–2.56 (m, 1H), 2.59–2.93 (m,2H), 3.4–3.83 (m, 1H), 4.39 ($q_{AB}$ J=9 Hz, 2H), 4.53–4.70 (m, 1H), 7.23 (s,5H), 7.18 (d, J= 6 Hz, 2H), 7.70 (d, J= 6 Hz, 2H).

Calculated values for $C_{23}H_{30}O_5S$: C, 66.00; H, 7.23; S, 7.66. Found: C, 65.81; H, 7.10; S, 7.47.

COMPOUND 16

(2S,3S)-2-O-Benzyl-3-O-tosyl-2,3,8-nonenetriol

A solution of aluminum hydride (30 mL, 15 mmol, 1M solution in THF), was added to epoxide [15] (3.143 g, 7.52 mmol) in dry ether (100 mL) at 0° C. The mixture was stirred at RT for 1 h and decomposed slowly by the addition of water (25 mL) and the aqueous solution was extracted with ether (4×50 mL). The combined ether extracts were dried ($MgSO_4$) and concentrated to furnish [16] (3 g, 95%). An analytical sample was obtained by silica gel column chromatography with hexane-EtOAc (7:3) as eluent: $^1H$ NMR ($CDCl_3$) delta 0.80–1.93 (m, 15H, $1D_2O$ exchangeable), 2.36 (s,3H), 3.30–3.96 (m,2H), 4.4 ($q_{AB}$ J= 7.5 Hz, 2H), 4.43–4.80 (m, 1H), 7.16 (d, J= 9 Hz, 2H), 7.23 (s,5H), 7.7 (d, J= 9 Hz, 2H).

Calculated values for $C_{23}H_{32}O_5S$: C, 65.69; H, 7.67; S, 7.62. Found: C, 65.90; H, 7.48; S, 7.49.

COMPOUND 17

(2S, 3S)-2-O-Benzyl-3-O-tosyl-8-O-tetrahydropyranyl-2,3,8-nonanetriol

A solution of alcohol [16] (2.8 g, 6.6667 mmol), and dihydropyran (1.68 g, 13,33 mmol) in dry $CH_2Cl_2$ (50 mL) containing pyridinium p-toluenesulfonate (PPTS, 0.33 g, 1.33 mmol) was stirred at RT for 4 h. The reaction mixture was diluted with ether and washed once with half saturated brine to remove the catalyst PPTS and dried ($MgSO_4$). The residue obtained after evaporation of the solvent was purified by silica gel column chromatography using hexane-EtOAc (95:5) as eluent, to afford [17] (3.3 g, 99%): $^1H$ NMR ($CDCl_3$) delta 0.65–2.03 (m,20H) 2.38 (s,3H), 3.18–4.11 (m,4H), 4.40 ($q_{AB}$ J= 9 Hz, 2H), 4.5–5.78 (m,2H), 7.18 (d, J 9 Hz, 2H), 7.26 (s,5H), 7.73 (d, J= 9 Hz, 2H).

Calculated values for $C_{28}H_{40}O_6S$: C, 66.64; H, 7.99; S, 6.35. Found: C, 66.45; H, 7.70; S, 6.51.

COMPOUND 18

(2S,3R)-3-Azido-2-O-benzyl-8-O-tetrahydropyranyl-2,8-nonanediol

Compound [8] was prepared from [17] following the procedure described for the formation of [4]. The crude product, after column chromatography (hexane-EtOAc, 95:5), gave pure [18] (82%): $^1H$ NMR ($CDCl_3$) delta 0.88–2.32 (m, 20H), 3.15–4.05 (m, 5H), 4.51 ($q_{AB}$ J= 10.5 Hz, 2H), 4.52–4.72 (m, 1H), 7.22 (s,5H).

Calculated values for $C_{21}H_{33}N_3O_3$: C, 67.17; H, 8.86; N, 11.19. Found: C, 67.07; H, 9.02; N, 11.31.

COMPOUND 19

(2S,3R)-3-Amino-2-O-benzyl-8-O-tetrahydropyranyl-2,3,8-nonanediol

The azide [18] was reduced by a procedure similar to that described for the preparation of [5], to afford the amine [19] quantitatively: $^1H$ NMR ($CDCl_3$) delta 0.76 1.23 (m, 22H, $2D_2O$ exchangeable) , 2.63–4.06 (m, 5H), 4.42 ($q_{AB}$ J= 7.5 Hz, 2H) , 4.46– 4.73 (m, 1H), 7.23 (s,5H).

Calculated values for $C_{21}H_{35}NO_3$: C, 72.17; H, 10.09; N, 4.01. Found: C, 72.34; H, 9.02; N, 4.16.

COMPOUND 20

5-Amino-6-chloro-4[2(S)-O-benzyl-8-O-tetrahydropyranyl-3(R)-2,8-dihydroxynonyl]aminopyrimidine Compound [20] was prepared from 19, by following the procedure described for the formation of [6]. The residue, obtained after solvent removal, was chromatographed over silica gel (EtOAc-hexanes 1:5) to give [20] (28%): $^1$H NMR (CDCl$_3$) delta 0.63–2.33 (m, 20H), 3.03–5.13 (m, 11H, 3D$_2$O exchangeable), 7.13 (s,5H), 7.83 (s,1H).

Calculated values for $C_{25}H_{37}N_4ClO_3$: C, 62.94; H, 7.82; N, 11.74; Cl, 7.43. Found: C, 63.22; H, 7.64; N, 11.94; Cl, 7.23.

COMPOUND 21

6-Chloro-9-[2(S)-O-benzyl-2,8-dihydroxy,3(R)-nonyl]purine

An acidified (conc. HCl, 0.15 mL) solution of [20] (0.3 g, 0.63 mmol) in TEOF (15 mL) was stirred at RT for 24 h. The residue obtained, after removal of TEOF, was dissolved in absolute ethanol (10 mL), containing PPTS (0.025 g) and refluxed for 1 h. Solvent was then removed under reduced pressure and the crude product was purified by silica gel column chromatography, using EtOAc-hexanes (3:1) to give [21] (0.15 g, 60%): $^1$H NMR (CDCl$_3$) delta 0.66–2.42 (m, 15H, 1D$_2$O exchangeable), 3.36–3.96 (m,2H), 4.4 (q$_{AB}$ J= 13.4 Hz, 2H), 4.46–4.79 (m, 1H), 7.19 (s,5H), 8.26 (s,1H), 8.62 (s,1H).

Calculated values for $C_{21}H_{27}O_2N_4Cl$: C, 62.60; H, 6.75; N, 13.91; Cl, 8.80. Found: C, 62.73; H, 6.82; N, 13.72; Cl, 8.69.

COMPOUND 22

9-[2(S)-O-Benzyl-2,8-dihydroxy-3(R)-nonyl]adenine

Amination of chloropurine derivative [21] was carried out as for the synthesis of [8] from [7]. Crude product, obtained after workup, was purified by silica gel column chromatography, eluting with MeOH-EtOAc (5:95) to give [22] (90%): $^1$H NMR (CDCl$_3$) delta 0.70–1.60 (m,12H), 1.63–2.33 (m,2H), 2.80 (bs, $^1$H, D$_2$O exchangeable), 3.33–4.00 (m,2H), 4.30 (q$_{AB}$ J= 13.5 Hz, 2H), 4.33– 4.66 (m, 1H), 6.23 (bs, 2H, D$_2$O exchangeable), 7.13 (s,5H), 7.83 (s,1H), 8.20 (s,1H).

Calculated values for $C_{21}H_{29}O_2N_5$: C, 65.77; H, 7.62; N, 18.26. Found: C, 65.47; H, 7.72; N, 18.04.

COMPOUND 23

9-[2(S), 8-Dihydroxy-3(R)-nonyl]adenine

Diol [23] was prepared in 90% yield by debenzylating [22] using the procedure described for [10]: $^1$H NMR (D$_2$O) 0.71–1.10 (m, 12H), 1.77–1.88 (m, 2H), 3.38–3.54 (m, $^1$H), 3.90–3.98 (m, $^1$H), 4.19–4.26 (m, 1H), 8.02 (s,1H), 8.08 (s,1H).

Calculated values for $C_{14}H_{23}O_2N_5$: C, 57.32; H, 7.90; N, 23.87. Found: C, 57.16; H, 7.83; N, 23.72.

This compound is the 8-dihydroxy analog of EHNA which was tested as described in Example 2 and shown to inhibit ADA activity.

EXAMPLE 2

Testing for ADA Inhibition

Compounds [10] (the 9-hydroxy analog), [23] (the 8-hydroxy analog), and [14] (the 8,9-dihydroxy analog) were tested for ADA inhibition activity, using calf intestinal ADA (Type III, Sigma Chemical Company) measured at 30° C. by direct spectrophotometric assays at 265 nm, as described in Harriman et al 1992. The Ki values were 3.4, 11, and 6, respectively, times $10^{-9}$.

EXAMPLE 3

Synthesis of Various Other Analogs of EHNA

Figure 4:
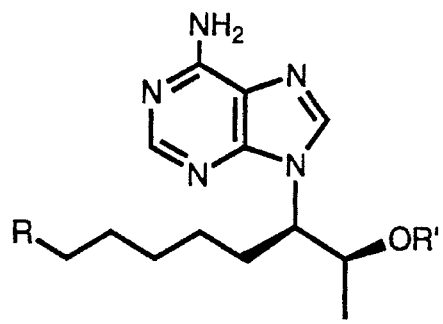
FIG. 4 depicts the reactions used to create other analogs of EHNA which have been modified by the addition of various non-hydroxy moieties at the #9 carbon atom.

This example and FIG. 4 depict the synthesis of several additional analogs of EHNA. Except as noted, the synthetic reactions described below used the benzyl-protected compound [9] (described in Example 1) as the starting reagent. Elemental and NMR analyses confirmed that each compound was created in analytically pure form, except as noted for compounds [26] and [28]. As described in Example 4, several of these analogs (Compounds [25], [25], [29], [31], and [32]) were tested for inhibition of the ADA enzyme, and were found to have a potency in the desired range.

COMPOUND 24

9-[9-Benzoyloxy-2(S)-O-benzyl-3(R)-nonyl]adenine

This analog, which has benzyl groups coupled to both the #2 and #9 carbon atoms, was prepared by adding n,n-diisopropylazodicarboxylate (DIAD, 202 mg, 1 mmol) to a stirred solution of compound [9] (314 mg, 0.82 mmol), benzoic acid (BzOH, 122 mg, 1 mmol), and triphenyl phosphine (PPh$_3$, 262 mg, 1 mmol) in THF (5 ml). The mixture was stirred at room temperature for 24 hr and precipitated triphenyl phosphine oxide was filtered out. The filtrate was concentrated and the residue was chromatographed on silica gel using ethyl acetate (EtOAc) to provide [24], which was further purified by preparative thin layer chromatography (TLC) using EtOAc and methanol (MeOH) at 9:1. Yield was 250 mg.

COMPOUND 25

9-[9-Benzoyloxy-2(S)-hydroxy-3(R)-nonyl]adenine

This alcohol, which has a benzyl group coupled to the #9 carbon atom but not the #2 carbon atom, was created by treating compound [24] (200 mg) in ethanol (EtOH, 18 ml) and cyclohexene (6 ml) with 20% palladium hydroxide on charcoal (PdOH$_2$/C, 0.15 g). The suspension was stirred at reflux for 12 hours. After cooling to room temperature, the mixture was filtered and the filtrate was concentrated at reduced pressure. The residue was chromatographed over silica (EtOAc and MeOH at 9:1) to give pure [25], 130 mg.

COMPOUND 26

9-[2(S)-O-benzyl-9-phthalimido-3(R)-nonyl]adenine

Compound [26] was created in the same way as compound [24], except that phthalimide was used in place of benzoic acid. Analytically pure compound could not be obtained, since it always contained traces of triphenyl phosphine oxide and dihydro-DIAD; it was used as a reagent in the next reaction.

COMPOUND 27

9-[2(S)-hydroxy-9-phthalimido-3(R)-nonyl]adenine

This alcohol was created in 85% yield, with [26] as the starting reagent, using the same palladium on charcoal (PdOH$_2$/C) catalytic procedure used to create [25].

COMPOUND 28

9-[2(S)-O-benzyl-9-chloro-3(R)-nonyl]adenine

Analog [28], with a benzyl ring on the #2 carbon atom and a chlorine atom coupled to the #9 carbon atom, was created by adding PPh$_3$ (400 mg, 1.5 mmol) to a stirred solution of [9] (500 mg, 1.3 mmol) and NaHCO$_3$ (50 mg) in anhydrous CCl$_4$ (5 ml). The mixture was treated at reflux for 12 hours, then filtered, and the filtrate was concentrated. The residue was chromatographed over silica gel (EtOAc) to provide a 75% yield. Analytically pure compound could not be obtained, since it contained traces of triphenyl phosphine oxide.

COMPOUND 29

9-[9-chloro-2(S)-hydroxy-3(R)-nonyl]adenine

This analog, with a halide moiety at the #9 carbon and an alcohol group at the #2 carbon atom, was prepared in 82% yield using [28] as the starting reagent and using the same palladium on charcoal (PdOH$_2$/C) catalytic procedure used to create [25].

COMPOUND 30

Methyl-7(R)-adenine-9-yl)-8(S)-O-benzyl-nonoate

Analog [30], with an ester group at the #9 carbon and a benzyl group at the #2 carbon, was created by adding pyridinium dichromate (PDC, 2.755 g, 7.3 mmol) to a solution of [9] (1.369 g, 3.4 mmol) in dimethyl formamide (DMF, 2 ml). The mixture was stirred at room temperature for 24 hours, then diluted with ethyl acetate and passed through a mixture of silica gel and Na$_2$SO$_4$ (1:1) to give the corresponding acid (220 mg, 15.7% yield). Esterification of the acid using methanol (MeOH) and H$_2$SO$_4$ gave a 66% yield.

COMPOUND 31

Methyl-7(R)-adenine-9-yl)-8(S)-hydroxy-nonoate

Analog [31], with an ester group at the #9 carbon and a hydroxy group at the #2 carbon, was created in 82% yield using the same palladium on charcoal (PdOH$_2$/C) catalytic procedure used to create [25], using the benzyl analog [30] as the starting reagent. Ester 31 can also be referred to as 9-[2(s)-hydroxy-9-carboxymethyl- 3(R)-nonyl]adenine

COMPOUND 32

9-[2(S)-hydroxy-3(R)-non-8-enyl]adenine

Unsaturated analog [32] was created by using the unsaturated benzyl-protected analog [7], shown in FIG. 3 and described in Example 1, as the starting reagent. Compound [7] (200 mg, 0.55 mmol) in toluene (10 ml) was cooled with dry ice/acetone and ammonia was bubbled through the solution until the volume of the mixture reached 40 ml. Sodium metal was added in portions with vigorous stirring until the mixture was neutralized with NH$_4$Cl and methanol and evaporated to dryness. The compound was then extracted with CH$_2$Cl$_2$ and the extracts were dried over Na$_2$SO$_4$ and evaporated. The product was purified by preparative TLC using ethyl acetate to give a 70% yield of [32].

EXAMPLE 4

Testing of Various Analogs for ADA Inhibition

Several of the analogs described in Example 3 were tested for inhibition of the adenosine deaminase (ADA) enzyme, using the procedures described in Example 2. They were found to have a potency in the desirable range, which indicates that they can inhibit the ADA enzyme without irreversibly poisoning it. The Ki values for Compounds [25], [25], [29], [31], and [32] were 0.2, 2.3, 3.7, 5.0, and 2.5, respectively, times $10^{-9}$.

EXAMPLE 5

Testing of 9-OH-EHNA for Protection Against Ischemic Damage to Tissue

After synthesis of the 9-hydroxy and 8-hydroxy analogs of EHNA, samples were provided by the Applicant to Dr. Robert Rodgers of the Department of Pharmacology and Toxicology at the University of Rhode Island. There were sufficient quantities of 9-hydroxy-EHNA for thorough testing as described below, while quantities of 8-hydroxy-EHNA were very small. Accordingly, most tests used 9-hydroxy-EHNA and compared it to unmodified EHNA and to disulfiram, an unrelated compound that is known to have certain protective anti-ischemic effects in cardiovascular tissue.

The tests carried out by Dr. Rodgers used a widely-used protocol known as a "Langendorf" preparation, which involves removing intact hearts from sacrificed lab animals (male Sprague-Dawley rats were used), and perfusing the hearts with liquids containing controlled quantities (or deficits) of oxygen and glucose for fixed periods of time. The procedures used in these experiments are described in detail in Davidoff and Rodgers, *Hypertension* 15:633–642 (1990), with certain minor modifications. The left atrium is filled at 15 cm H$_2$O pressure, and the left ventricle ejects into a buffer-filled column against a pressure which equates to 72 mm Hg, except during ischemic periods. The perfusate was Krebs-Henseleit buffer with HCO$_3$ (25 mM), Ca$^{++}$(2.2 mM), and glucose (10 mM). When gassed with 95% O$_2$ and 5% CO$_2$, the pH of the perfusate was 7.4±0.2. Pefusate and ambient temperatures were held at 37° C. and the hearts were allowed to beat spontaneously.

After perfusion began, the isolated hearts were allowed to stabilize for 10 minutes, then they were treated for 10 minutes with one of the test drugs (EHNA, 9-hydroxy-EHNA, or disulfiram) or buffered saline containing either dilute ethyl alcohol (used to increase the solubility of EHNA or 9-hydroxy-EHNA) or dilute dimethyl sulfoxide (used to increase solubility of disulfiram). Following stabilization and treatment, the hearts were subjected to simulated ischemia for 20 minutes; no oxygen was added to the perfusate during this period. When the ischemic period ended, oxygen was again added to the perfusion buffer, and the following parameters were measured over a period of 10 minutes:

LVPP—left ventricular pulse pressures (time-dependent pressures, calculated as peak pressure minus diastolic pressure, in mm Hg, millimeters of mercury column)

LVEDP—left ventricular end diastolic pressure (i.e, time-dependent pressures as the ventricle relaxed during diastolic filling, in mm Hg)

CFR—coronary flow rate (mL/min)

HR—spontaneous heartbeat rate (beats/min)

ECG—electrocardiogram (surface potential, in mV)

The results indicated that both EHNA and 9-hydroxy-EHNA reduced the incidence of fibrillation, as shown in Table 1

TABLE 1

|          | Total # | # fibrillating | % fibr. |
|----------|---------|----------------|---------|
| Controls | 13      | 4              | 31      |
| EHNA     | 7       | 1              | 14      |
| 9-OH—EHNA| 9       | 1              | 11      |
| Disulfiram | 5     | 2              | 40      |

Both EHNA and 9-OH-EHNA caused a moderate increase in both LVPP and in coronary flow rate after ischemia.

The most important difference observed between EHNA and 9-OH-EHNA appeared in measurements of LVEDP (left ventricular end diastolic pressure). This parameter indicates whether the muscles of the left ventricular wall are able to relax promptly following contraction. Prompt relaxation is essential, since it allows the ventricle to fill with blood during diastolic relaxation, between contractions. A high LVEDP level is very undesirable, since it indicates that the heart muscle has become stiffened by ischemic damage and no longer has sufficient flexibility and elasticity to properly fill the chambers with blood during diastole. In the tests carried out, 9-OH-EHNA provided a significantly higher level of protection against muscle stiffening than unmodified EHNA.

This useful biological activity could not have been predicted prior to the experiments, and it helps overcome any presumption of obviousness of hydroxylated analogs based upon prior art concerning EHNA.

Thus, there has been shown and described a new class of EHNA analogs having modified side chains, which are useful in inhibiting ADA activity; also disclosed herein are methods of synthesizing such analogs, and methods of using such analogs as adjuncts during anti-cancer or anti-viral chemotherapy. Although this invention has been exemplified for purposes of illustration and description by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention.

REFERENCES

Abushanab, E., et al, "Practical Enantiospecific Synthesis of (+) -erythro-9-(2-Hydroxy-3-nonyl) adenine," *Tetrahedron Lett.* 25: 3841 (1984)

Abushanab, E., et al, "The Chemistry of L-Ascorbic and Disoascorbic Acids: 1. The Preparation of Chiral Butanetriols and -tetrols" *J. Org. Chem.* 53:2598–2602 (1988)

Bastian, G., et al, "Adenosine Deaminase Inhibitors: Conversion of a Single Chiral Synthon into erythro- and threo-9-(2-hydroxy- 3-nonyl)adenines," *J. Med. Chem.* 24:1383–1385 (1981)

Baker, D. C., and Hawkins, L. D., "Synthesis of Inhibitors of Adenosine Deaminase: A Total Synthesis of erythro-3-(Adenin-9-yl)- 2-nonanol and Its Isomers from Chiral Precursors," *J. Org . Chem.* 47:2179–2184 (1982)

Cristalli, G., et al, "Adenosine Deaminase Inhibitors: Synthesis and Biological Activity of Deaza Analogues of erythro-9-(2-Hydroxy- 3-nonyl)adenine," *J. Med Chem.* 31: 390–397 (1988) .

Cristalli, G., et al, "Adenosine Deaminase Inhibitors: Synthesis and Structure-Activity Relationships of Imidazole Analogues of erythro-9- (2-Hydroxy-3nonyl) adenine," *J. Med. Chem.* 34: 1187– 1192 (1991)

Harriman, G. C. B., et al, "Adenosine Deaminase Inhibitors: Synthesis and Biological Evaluation of Cl' and Nor-Cl' Derivatives of (+)-erythro-9-(2(S)-Hydroxy-3(R)-nonyl)adenine," *J. Med. Chem.* 35:4180–4184 (1992)

Lambe, C. U., and Nelson, D. J., "Pharmacokinetics of Inhibition of Adenosine Deaminase by erythro-9-(2-hydroxy-3-nonyl)adenine in CBA Mice," *Biochem. Pharmacol.* 31:535–539 (1982)

McConnell, W. R., et al, "Metabolism and Disposition of erythro-9-( 2-Hydroxy-3-nonyl)[$^{14}$C]adenine in the Rhesus Monkey," *Drug Metab. Disp.* 8:5–7 (1980)

Schaeffer, H. J. and Schwender, C. F., "Enzyme Inhibitors XXVI: Bridging Hydrophobic and Hydrophilic Regions on Adenosine Deaminase with some 9-(2-Hydroxy-3-alkyl)adenines," *J. Med. Chem.* 17: 6–8 (1974)

I claim:

1. A compound selected from the group consisting of:
   (a) 9-[2(S),9-dihydroxy-3(R)-nonyl]adenine;
   (b) pharmacologically acceptable salts thereof;
   (c) pharmacologically acceptable isomers thereof which inhibit adenosine deaminase activity with a Ki value between about $10^{-7}$ and about $10^{-10}$; and,
   (d) pharmacologically acceptable analogs thereof which have a chemical moiety, other than hydrogen or a hydroxy group, bonded to the number 9 carbon atom on the side chain and which inhibit adenosine deaminase activity with a Ki value between about $10^{-7}$ to about $10^{-10}$.

2. A compound of claim 1 consisting of an analog of 9-[ 2(S),9-dihydroxy-3(R)-nonyl]adenine wherein the chemical moiety bonded to the number 9 carbon atom on the side chain is selected from the group consisting of:
   (a) halides;
   (b) carboxylic acids and salts thereof;
   (c) azide moieties;
   (d) moieties which are coupled to the number 9 carbon atom on the side chain via ester linkages and which do not substantially alter the affinity of the analog for adenosine deaminase, thereby allowing an analog with an ester linkage to have a Ki value for adenosine deaminase inhibition which remains within the range of about $10^{-7}$ to about $10^{-10}$; and,
   (e) moieties which are coupled to the number 9 carbon atom on the side chain via ether linkages and which do not substantially alter the affinity of the analog for adenosine deaminase, thereby allowing an analog with an ether linkage to have a Ki value for adenosine deaminase inhibition which remains within the range of about $10^{-7}$ to about $10^{-10}$.

3. A compound selected from the group consisting of:
   (a) 9-[2(S),8-dihydroxy-3(R)-nonyl]adenine;
   (b) pharmacologically acceptable salts thereof;
   (c) pharmacologically acceptable isomers thereof which inhibit adenosine deaminase activity with a Ki value between about $10^{-7}$ to about $10^{-10}$; and, (d) pharmacologically acceptable analogs thereof which have a chemical moiety, other than hydrogen or a hydroxy group, bonded to the number 9 carbon atom on the side chain and which inhibit adenosine deaminase activity with a Ki value between about $10^{-7}$ to about $10^{-10}$.

4. A compound of claim 1 consisting of an analog of 9-[2(S),8-dihydroxy-3(R)-nonyl]adenine wherein the chemical moiety bonded to the number 8 carbon atom on the side chain is selected from the group consisting of:

(a) halides;

(b) carboxylic acids and salts thereof;

(c) azide moieties;

(d) moieties which are coupled to the number 9 carbon atom on the side chain via ester linkages and which do not substantially alter the affinity of the analog for adenosine deaminase, thereby allowing an analog with an ester linkage to have a Ki value for adenosine deaminase inhibition which remains within the range of about $10^{-7}$ to about $10^{-10}$; and, (e) moieties which are coupled to the number 9 carbon atom on the side chain via ether linkages and which do not substantially alter the affinity of the analog for adenosine deaminase, thereby allowing an analog with an ether linkage to have a Ki value for adenosine deaminase inhibition which remains within the range of about $10^{-7}$ to about $10^{-10}$.

5. A compound which is an analog of erythro-hydroxynonyladenine, consisting of an erythro-hydroxynonyl side chain attached to an adenyl structure, wherein the erythro-hydroxynonyl side chain has been modified by bonding at least one moiety which normally is not present in erythro-hydroxynonyladenine to a carbon atom other than carbon atoms designated as number 8 or number 9 when conventional numbering is used, wherein the moiety coupled to such carbon atom other than the number 8 and number 9 carbon atoms does not substantially alter the affinity of the analog for adenosine deaminase, thereby allowing the analog of erythro-hydroxynonyladenine to function as a pharmacologically acceptable inhibitor of adenosine deaminase with a Ki value that remains within the range of about $10^{-7}$ to about $10^{-10}$.

6. The compound of claim 5 wherein said moiety is selected from the group consisting of:

(a) halides;

(b) carboxylic acids and salts thereof;

(c) azide moieties;

(d) moieties which are coupled to a carbon atom on the erythro-hydroxynonyl side chain other than the number 9 and number 8 carbon atoms via ester linkages, and which do not substantially alter the affinity of the analog for adenosine deaminase;

(e) moieties which are coupled to a carbon atom on the erythro-hydroxynonyl side chain other than the number 9 and number 8 carbon atoms via ether linkages, and which do not substantially alter the affinity of the analog for adenosine deaminase.

7. The compound of claim 5 wherein at least one second moiety is also attached to the erythro-hydroxynonyl side chain through a carbon atom designated as number 8 or number 9 when conventional numbering is used.

8. A method of synthesizing a hydroxylated analog of erythro-hydroxynonyladenine in which an erythro-hydroxynonyl side chain attached to an adenyl structure has been modified by addition of at least one moiety that normally is not present in erythro-hydroxynonyladenine, comprising the following steps:

a. reacting an epoxide reagent having a desired chiral orientation with an alkyl halide reagent having an unsaturated bond between two selected carbon atoms, under conditions which cause said reagents to create an unsaturated aliphatic compound comprising a first portion having a desired chiral orientation and a second portion having an unsaturated bond;

b. reacting the unsaturated aliphatic compound with at least one third reagent under conditions which cause said third reagent to modify the unsaturated aliphatic compound by adding at least one hydroxyl group to at least one of the two carbon atoms which previously were bonded to each other by the unsaturated bond, thereby creating a hydroxylated saturated aliphatic compound;

c. completing any additional steps necessary to remove any protective groups and to finish synthesizing the hydroxylated analog of erythro-hydroxynonyladenine; and, d. purifying said hydroxylated analog of erythro-hydroxynonyladenine.

9. The method of claim 8 wherein said epoxide reagent is selected from the group consisting of 1,2-epoxybutane and derivatives thereof, and wherein said alkyl halide reagent is a pentenyl compound having a reactive halide moiety.

10. A method of inhibiting adenosine deaminase activity in a patient in need thereof, wherein the patient is receiving a therapeutic drug that is degraded by adenosine deaminase in the absence of an adenosine deaminase inhibitor, comprising administering to the patient a therapeutically effective quantity of a pharmacologically acceptable analog of erythro-hydroxynonyladenine in which an erythro-hydroxynonyl side chain has been modified by addition of at least one moiety that normally is not present in erythro-hydroxynonyladenine, wherein said analog is a pharmacologically acceptable inhibitor of adenosine deaminase.

11. The method of claim 10 wherein the analog of erythro-hydroxynonyladenine has a binding affinity for adenosine deaminase which is reflected by a Ki value in the range of about $10^{-10}$ to about $10^{-7}$.

12. The method of claim 10 wherein at least one of said moieties comprises a hydroxyl moiety.

13. The method of claim 10 wherein at least one of said moieties is selected from the group consisting of:

(a) halides;

(b) carboxylic acids and salts thereof;

(c) azide moieties;

(d) moieties which are coupled to the erythro-hydroxynonyl side chain via ester linkages and which do not substantially alter the affinity of the-analog for adenosine deaminase, thereby allowing an analog with an ester linkage to have a Ki value for adenosine deaminase inhibition which remains within the range of about $10^{-7}$ to about $10^{-10}$; and, (e) moieties which are coupled to the erythro-hydroxynonyl side chain via ether linkages and which do not substantially alter the affinity of the analog for adenosine deaminase, thereby allowing an analog with an ether linkage to have a Ki value for adenosine deaminase inhibition which remains within the range of about $10^{-7}$ to about $10^{-10}$.

\* \* \* \* \*